US007867775B2

(12) United States Patent
Röder et al.

(10) Patent No.: US 7,867,775 B2
(45) Date of Patent: Jan. 11, 2011

(54) SELECTION OF HEAD AND NECK CANCER PATIENTS FOR TREATMENT WITH DRUGS TARGETING EGFR PATHWAY

(75) Inventors: Heinrich Röder, Steamboat Springs, CO (US); Maxim Tsypin, Steamboat Springs, CO (US); Julia Grigorieva, Steamboat Springs, CO (US)

(73) Assignee: Biodesix, Inc., Steamboat Springs, CO (US)

( * ) Notice: Subject to any disclaimer, the term of this patent is extended or adjusted under 35 U.S.C. 154(b) by 0 days.

(21) Appl. No.: 12/321,393

(22) Filed: Jan. 20, 2009

(65) Prior Publication Data

US 2009/0171872 A1  Jul. 2, 2009

Related U.S. Application Data

(63) Continuation-in-part of application No. 11/396,328, filed on Mar. 31, 2006.

(51) Int. Cl.
*G01N 24/00* (2006.01)

(52) U.S. Cl. .................... 436/173; 436/86; 436/171; 435/6; 435/69.9; 435/372; 702/20; 702/179

(58) Field of Classification Search ........................ None
See application file for complete search history.

(56) References Cited

U.S. PATENT DOCUMENTS

| 7,736,905 B2 | 6/2010 | Roder et al. ................ 436/173 |
| 2005/0048547 A1 | 3/2005 | Zhao et al. .................... 435/6 |
| 2005/0164218 A1 | 7/2005 | Agus et al. .................... 435/6 |
| 2005/0267689 A1 | 12/2005 | Tsypin ........................ 702/19 |
| 2006/0029574 A1 | 2/2006 | Albitar et al. ............... 424/93.1 |
| 2007/0231921 A1 | 10/2007 | Röder et al. ................ 436/173 |
| 2009/0171872 A1 | 7/2009 | Roder et al. .................. 706/12 |

FOREIGN PATENT DOCUMENTS

| WO | WO 2004/012588 | 2/2004 |
| WO | WO 2005/010492 | 2/2005 |
| WO | WO 2005/098445 | 10/2005 |
| WO | WO2007/109571 | 9/2007 |

OTHER PUBLICATIONS

Written Opinion of the International Searching Authority in PCT/US2007/007467 dated Nov. 8, 2007.
International Search Report in PCT Application Publication No. WO 2007/126758, published Nov. 8, 2007.
Fleming et al. "Windowed mass selection method: a new data processing algorithm for liquid chromatography-mass spectrometry data", Journal of Chromatography A, vol. 849, pp. 71-85 (1999).

(Continued)

*Primary Examiner*—Yelena G. Gakh
*Assistant Examiner*—Robert Xu
(74) *Attorney, Agent, or Firm*—McDonnell Boehnen Hulbert & Berghoff LLP

(57) ABSTRACT

Methods using mass spectral data analysis and a classification algorithm provide an ability to determine whether a head and neck squamous cell carcinoma (HNSCC) patient is likely to benefit from a drug targeting an epidermal growth factor receptor pathway, including small molecule epidermal growth factor receptor tyrosine kinase inhibitors (EGFR-TKIs) and monoclonal antibody EGFR inhibitors.

5 Claims, 2 Drawing Sheets

OTHER PUBLICATIONS

Senko et al., "Determination of monoisotopic masses and ion population for large biomolecules from resolved isotopic distribution", Journal of the American Society for Mass Spectrometry, vol. 6, pp. 229-233 (1995).

Gras et al., "Improving protein identification from peptide mass fingerprinting through a parameterized multi-level scoring algorithm and an optimized peak detection", Electrophoresis, vol. 20, pp. 3535-3550 (1999).

Metro, et al., "Epidermal Growth Factor Receptor (EGFR) Targeted Therapies in Non-Small Cell Lung Cancer (NSCLC)", Reviews on Recent Clinical Trials, vol. 1, No. 1, pp. 1-13 (2006).

Taguchi, et al., "Mass Spectrometry to Classify Non-Small-Cell Lung Cancer Patients for Clinical Outcome after, Treatment with Epidermal Growth Factor Receptor Tyrosine Kinase Inhibitors: A Multicohort Cross-Institutional Study", Journal of the National Cancer Institute, vol. 99, Issue 11, pp. 838-846 (2007).

Ladanyi, et al., "Lung adenocarcinoma: guiding EGFR-targeted therapy and beyond", Modern Pathology, vol. 21, pp. S16-S22 (2008).

Office Action dated Feb. 6, 2009 in U.S. Appl. No. 11/396,328, filed Mar. 31, 2006.

Amendment and pending claims filed Apr. 7, 2009 in U.S. Appl. No. 11/396,328, filed Mar. 31, 2006.

U.S. Appl. No. 12/321,394, filed Jan. 20, 2009.

U.S. Appl. No. 12/321,392, filed Jan. 20, 2009.

Extended European Search Report in EP 07754043.3, dated Jun. 8, 2009.

U.S. Office Action dated Aug. 25, 2009 in U.S. Appl. No. 11/396,328, filed Mar. 31, 2006.

Lynch et al., *Activating Mutations in the Epidermal Growth Factor Receptor Underlying Responsiveness of Non-Small-Cell Lung Cancer to Gefitinib*, The New England Journal of Medicine, vol. 350, No. 21, pp. 2129-2139 (2004).

Alfassi, *On the Normalization of a Mass Spectrum for Comparison of Two Spectra*, American Society for Mass Spectrometry, vol. 15, pp. 385-387 (2004).

Bhanot et al., *A Robust Meta-Classification Strategy for Cancer Detection from MS Data*, Proteomics, vol. 6, pp. 592-604 (2006).

Koenker et al., *Quantile Smoothing Splines*, Biometrika vol. 81, pp. 673-680 (1994).

Eilers, *Parametric Time Warping*, Analytical Chemistry, vol. 76, No. 2, pp. 401-411 (2004).

Howard et al. *Identification and validation of a potential lung cancer serum biomarker detected by matrix-assisted laser desorption/ionization-time of flight spectra analysis*, Proteomics vol. 3, pp. 1720-1724 (2003).

International Search Report and Written Opinion mailed Feb. 17, 2010 in PCT/US2009/006269, filed Nov. 20, 2009.

Gourin et al., *Serum Protein Profile Analysis Following Definitive Treatment, in Patients with Head and Neck Squamous Cell Carcinoma*, Archives of Otolaryngology—Head and Neck Surgery, vol. 133 No. 11 pp. 1125-1130 (2007).

Diaz et al., *Current aspects of targeted therapy in head and neck tumors*, European Archives of Oto-Rhino-Laryngology, vol. 265 No. suppl. 1 pp. S3-S12 (2008).

Oda et al., *A comprehensive pathway map of epidermal growth factor receptor signaling*, Molecular Systems Biology, vol. 1 pp. 1-17(2005).

Duncan et al., *Quantitative matrix-assisted laser desorption/ionization mass spectrometry*, Briefings in Functional Genomics and Proteomics—Special Issue: Topics in Quantitative Biological Mass Spectrometry, vol. 7 No. 5 pp. 355-370 (2008).

International Preliminary Report on Patentability dated May 25, 2010 in PCT/US2009/006269 filed Nov. 20, 2009.

Extended European Search Report dated Aug. 25, 2010 in European Application No. 10003343.0.

Bhanot et al. *A robust meta-classification strategy for cancer detection from MS data Proteomics,* vol. 6, NR 2, pp. 592-607 (Jan. 2006).

Reyzer et al. *Maldi mass spectrometry for direct tissue analysis: a new tool for biomarker discovery*, Journal of Proteome Research vol. 4, No. 4, pp. 1138-1142 (2005).

Yanagisawa et al. *Proteomic patterns of tumour subsets in non-small-cell lung cancer*, The Lancet, vol. 362, pp. 433-439 (Aug. 9, 2003).

SELECTION OF HEAD AND NECK CANCER PATIENTS FOR TREATMENT WITH DRUGS TARGETING EGFR PATHWAY

CROSS-REFERENCE TO RELATED APPLICATIONS

This application is a continuation-in-part of our prior U.S. patent application Ser. No. 11/396,328 filed Mar. 31, 2006, currently pending, published as U.S. patent publication No. 2007/0231921. The entire content of the '121 patent application publication is incorporated by reference herein.

BACKGROUND

This invention relates to the field of identifying cancer patients as being likely to benefit from treatment with drugs targeting the epidermal growth factor receptor (EGFR) pathway. The identification for initial selection for treatment involves mass spectral analysis of blood samples from the patient in conjunction with a classification algorithm using a training set of class-labeled spectra from other patients with the disease.

Non-Small-Cell Lung Cancer (NSCLC) is a leading cause of death from cancer in both men and women in the United States. There are at least four (4) distinct types of NSCLC, including adenocarcinoma, squamous cell, large cell, and bronchioalveolar carcinoma. Squamous cell (epidermoid) carcinoma of the lung is a microscopic type of cancer most frequently related to smoking. Adenocarcinoma of the lung accounts for over 50% of all lung cancer cases in the U.S. This cancer is more common in women and is still the most frequent type seen in non-smokers. Large cell carcinoma, especially those with neuroendocrine features, is commonly associated with spread of tumors to the brain. When NSCLC enters the blood stream, it can spread to distant sites such as the liver, bones, brain, and other places in the lung.

Treatment of NSCLC has been relatively poor over the years. Chemotherapy, the mainstay treatment of advanced cancers, is only marginally effective, with the exception of localized cancers. While surgery is the most potentially curative therapeutic option for NSCLC, it is not always possible depending on the stage of the cancer.

Recent approaches for developing anti-cancer drugs to treat the NSCLC patients focus on reducing or eliminating the ability for cancer cells to grow and divide. These anti-cancer drugs are used to disrupt the signals to the cells to tell them whether to grow or die. Normally, cell growth is tightly controlled by the signals that the cells receive. In cancer, however, this signaling goes wrong and the cells continue to grow and divide in an uncontrollable fashion, thereby forming a tumor. One of these signaling pathways begins when a chemical in the body, called epidermal growth factor, binds to a receptor that is found on the surface of many cells in the body. The receptor, known as the epidermal growth factor receptor (EGFR) sends signals to the cells, through the activation of an enzyme called tyrosine kinase (TK) that is found within the cells. The signals are used to notify cells to grow and divide.

The use of targeted therapies in oncology has opened new opportunities to improve treatment options in advanced stage solid tumors where chemotherapy was previously the only viable option. For example, drugs targeting the epidermal growth factor receptor (EGFR) pathway (including without limitation, Tarceva (erlotinib), Erbitux (cetuximab), Iressa (gefitinib)) have been approved or are in evaluation for treatment of advanced stage solid tumors in particular non-small cell lung cancer (NSCLC). Metro G et al, Rev Recent Clin Trials. 2006 January; 1(1): 1-13.

One limitation of nearly all systemic cancer therapies is that a single agent will be active in only a minority of patients. As the field of targeted therapies evolves, it is becoming apparent that predictive biomarkers are integral to the success of any given therapy. In fact, many agents that have been recently approved by the regulatory authorities have been in diseases that harbor a universal molecular alteration, and thus a de facto predictive marker (e.g. imatinib in chronic myelogenous leukemia), or in conjunction with an assay to select patients (e.g. trastuzumab in HER2 positive breast cancer). By the same token, administering a targeted agent to an unselected patient population is usually accompanied by a modest to nonexistent response rate (e.g. gefitinib 250 mg in HNSCC). Ostensibly the successful development of any drug should be linked to predictors of its efficacy as these markers would markedly increase the likelihood that an individual patient will benefit. Given the morbidity and burden of treating cancer patients with ineffective agents, it is imperative that these endeavors are undertaken.

While in some trials EGFR-Inhibitors (EGFR-I) have been shown to generate sufficient survival benefit even in unselected populations, in others there was no substantial benefit. This lead AstraZeneca to withdraw their EGFR-tyrosine kinase inhibitor (TKI) (gefitinib, Iressa) from the United States market. Even in the case of approved EGFR-Is it has become more and more clear that efficient and reliable tests are necessary to identify those patients that might benefit from treatment with EGFR-Is vs. those that are not likely to benefit. Ladanyi M, et al., Mod Pathol. 2008 May; 21 Suppl 2:S16-22.

In our prior U.S. patent application Ser. No. 11/396,328, published as U.S. patent publication No. 2007/0231921, we have shown that a simple serum-based pre-treatment test using mass spectrometry and sophisticated data analysis techniques using a classifier and a training set of class-labeled spectra from other patients with the disease has promise for patient selection for treatment with drugs targeting the EGFR pathway in non-small cell lung cancer patients. See also Taguchi F. et al, JNCI 2007 v99(11), 838-846, the content of which is incorporated by reference herein. The test, called VeriStrat in its commercial version, assigns the label "VeriStrat good" or "VeriStrat poor" to pre-treatment serum or plasma samples. It has been shown in the JNCI paper that "VeriStrat good" patients are more likely to benefit from EGFR-I treatment than VeriStrat poor patients with a hazard ratio of "VeriStrat good" vs. "VeriStrat poor" patients of approximately 0.5.

Head and neck squamous cell carcinoma is used here to refer to a variety of cancer characterized by squamous cell carcinomas of the oral cavity, pharynx and larynx, salivary glands, paranasal sinuses and nasal cavity, as well as the lymph nodes of the upper part of the neck. Head and neck cancers account for approximately 3 to 5 percent of all cancers in the United States. These cancers are more common in men and in people over age 50. Tobacco (including smokeless tobacco) and alcohol use are the most important risk factors for head and neck cancers, particularly those of the oral cavity, oropharynx, hypopharynx and larynx. Eighty-five percent of head and neck cancers are linked to tobacco use.

SUMMARY OF THE INVENTION

We have discovered that the methods of mass spectral analysis of patient samples and classification using a training set described in our prior patent application provide not only a selection tool for initially identifying NSCLC patients as being likely to benefit from drugs targeting the EGFR pathway, but also that the methods provide a selection tool for selection of head and neck squamous cell carcinoma (HNSCC) cancer patients for treatment by such drugs.

We have further determined that the selection (including the selection for NSCLC patients and HNSCC patients) for such treatment applies to the two main classes of EGFR inhibitors (EGFR-I), namely (1) small molecule tyrosine kinase inhibitors (TKIs) such as getfitinib and erlotinib, and (2) monoclonal antibody EGFG-I such as cetuximab (Erbitux) and panitumumab.

Additionally, as the methods of this disclosure require only simple blood samples, the methods enable a fast and non-intrusive way of selection of such patients.

In one specific embodiment, a method is disclosed of determining whether a HNSCC patient is likely to benefit from treatment with a drug targeting the EGFR pathway (e.g., an EGFR-TKI such Tarceva (erlotinib); Erbitux (cetuximab), Iressa (gefitinib), or equivalent) comprising the steps of:

a) obtaining a mass spectrum from a sample from the patient;

b) performing one or more predefined pre-processing steps on the mass spectrum obtained in step a);

c) obtaining values of selected features in said spectrum at one or more predefined m/z ranges after the pre-processing steps on the mass spectrum in step b) have been performed;

d) using the values obtained in step c) in a classification algorithm using a training set comprising class-labeled spectra produced from samples from other patients to identify the patient as likely to benefit with treatment with the said drug.

DETAILED DESCRIPTION

We have examined the MS profiles from serum or plasma samples from recurrent and/or metastatic NSCLC and HNSCC patients who were treated with gefitinib, erlotinib or cetuximab as monotherapy, or combination regimens containing the EGFR-I, as well as samples from patients who were not treated with EGFR-I. The MALDI mass spectra were obtained from each sample and each patient was classified into "good" or "poor" outcome groups for survival comparison. We have found that the MS profile was predictive of survival outcomes in all EGFRI-treated cohorts, but not in the control cohorts.

Figure 1:
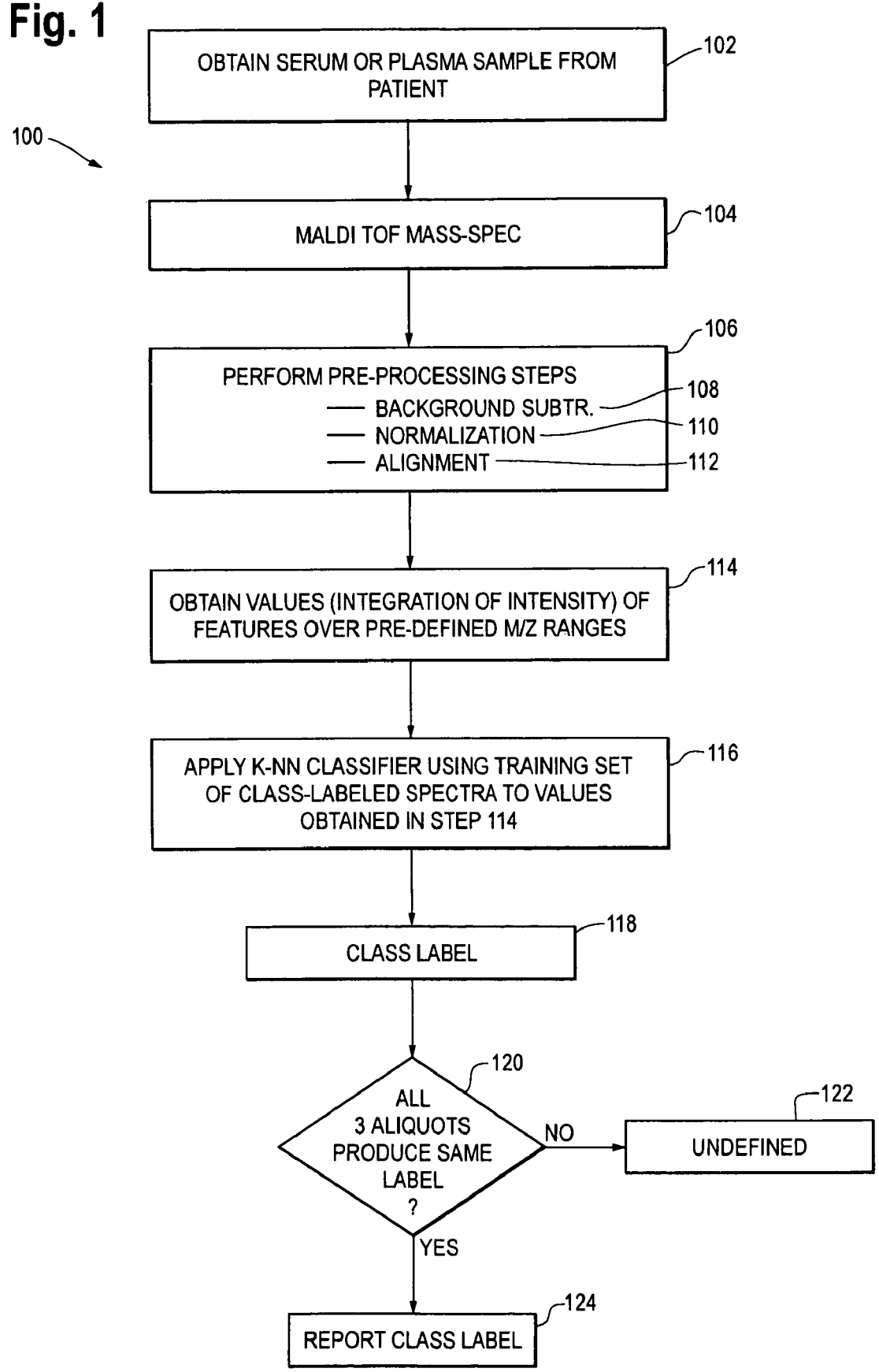
FIG. 1 is a flow chart showing a method for selection of HNSCC cancer patients for treatment with EGFR-I in accordance with a preferred embodiment of this invention.

The methods for selection of NSCLC and HNSCC patients for treatment with EGFR-I targeting is illustrated in flow chart form in FIG. 1 as a process 100.

At step 102, a serum or plasma sample is obtained from the patient. In one embodiment, the serum samples are separated into three aliquots and the mass spectroscopy and subsequent steps 104, 106 (including sub-steps 108, 110 and 112), 114, 116 and 118 are performed independently on each of the aliquots.

At step 104, the sample is subject to mass spectroscopy. A preferred method of mass spectroscopy is matrix assisted laser desorption ionization (MALDI) time of flight (TOF) mass spectroscopy, but other methods are possible. Mass spectroscopy produces data points that represent intensity values at a multitude of mass/charge (m/z) values, as is conventional in the art. In one example embodiment, the samples are thawed and centrifuged at 1500 rpm for five minutes at four degrees Celsius. Further, the serum samples may be diluted 1:10, or 1:5, in MilliQ water. Diluted samples may be spotted in randomly allocated positions on a MALDI plate in triplicate (i.e., on three different MALDI targets). After 0.75 ul of diluted serum is spotted on a MALDI plate, 0.75 ul of 35 mg/ml sinapinic acid (in 50% acetonitrile and 0.1% trifluoroacetic acid (TFA)) may be added and mixed by pipetting up and down five times. Plates may be allowed to dry at room temperature. It should be understood that other techniques and procedures may be utilized for preparing and processing serum in accordance with the principles of the present invention.

Mass spectra may be acquired for positive ions in linear mode using a Voyager DE-PRO or DE-STR MALDI TOF mass spectrometer with automated or manual collection of the spectra. Seventy five or one hundred spectra are collected from seven or five positions within each MALDI spot in order to generate an average of 525 or 500 spectra for each serum specimen. Spectra are externally calibrated using a mixture of protein standards (Insulin (bovine), thioredoxin (*E. coli*), and Apomyglobin (equine)).

At step 106, the spectra obtained in step 104 are subject to one or more pre-defined pre-processing steps. The pre-processing steps 106 are implemented in a general purpose computer using software instructions that operate on the mass spectral data obtained in step 104. The pre-processing steps 106 include background subtraction (step 108), normalization (step 110) and alignment (step 112). The step of background subtraction preferably involves generating a robust, asymmetrical estimate of background in the spectrum and subtracts the background from the spectrum. Step 108 uses the background subtraction techniques described in U.S. published applications 2007/0231921 and U.S. 2005/0267689, which are incorporated by reference herein. The normalization step 110 involves a normalization of the background subtracted spectrum. The normalization can take the form of a partial ion current normalization, or a total ion current normalization, as described in our prior patent application U.S. 2007/0231921. Step 112 aligns the normalized, background subtracted spectrum to a predefined mass scale, as described in U.S. 2007/0231921, which can be obtained from investigation of the training set used by the classifier.

Once the pre-processing steps 106 are performed, the process 100 proceeds to step 114 of obtaining values of selected features (peaks) in the spectrum over predefined m/z ranges. Using the peak-width settings of a peak finding algorithm, the normalized and background subtracted amplitudes may be integrated over these m/z ranges and assigned this integrated value (i.e., the area under the curve between the width of the feature) to a feature. For spectra where no peak has been detected within this m/z range, the integration range may be defined as the interval around the average m/z position of this feature with a width corresponding to the peak width at the current m/z position. This step is also disclosed in further detail in our prior patent application U.S. 2007/0231921.

At step 114, as described in our patent application published as US 2007/0231921, the integrated values of features in the spectrum is obtained at one or more of the following m/z ranges:

5732 to 5795

5811 to 5875

6398 to 6469

11376 to 11515

11459 to 11599

11614 to 11756

11687 to 11831

11830 to 11976

12375 to 12529

23183 to 23525

23279 to 23622 and 65902 to 67502.

In a preferred embodiment, values are obtained at least eight of these m/z ranges, and more preferably at all 12 of these ranges. The significance, and methods of discovery of these peaks, is explained in the prior patent application publication U.S. 2007/0231921.

At step 116, the values obtained at step 114 are supplied to a classifier, which in the illustrated embodiment is a K-nearest neighbor (KNN) classifier. The classifier makes use of a training set of class labeled spectra from a multitude of other patients (NSCLC or HNSCC cancer patients). The application of the KNN classification algorithm to the values at 114 and the training set is explained in our patent application publication U.S. 2007/0231921. Other classifiers can be used, including a probabilistic KNN classifier or other classifier.

At step 118, the classifier produces a label for the spectrum, either "good", "poor" or "undefined". As mentioned above, steps 104-118 are performed in parallel on three separate aliquots from a given patient sample. At step 120, a check is made to determine whether all three aliquots produce the same class label. If not, an undefined result is returned as indicated at step 122. If all aliquots produce the same label, the label is reported as indicated at step 124.

If the label reported at step 124 is "good" it indicates that the patient is likely to benefit from administration of the EGFR pathway targeting drug, or continued administration in the case of monitoring a patient in the course of treatment. If the label reported at step 124 is "poor" it indicates that the patient is not likely to benefit from treatment by such a drug.

It will be understood that steps 106, 114, 116 and 118 are typically performed in a programmed general purpose computer using software coding the pre-processing step 106, the obtaining of spectral values in step 114, the application of the KNN classification algorithm in step 116 and the generation of the class label in step 118. The training set of class labeled spectra used in step 116 is stored in memory in the computer or in a memory accessible to the computer.

Figure 2:
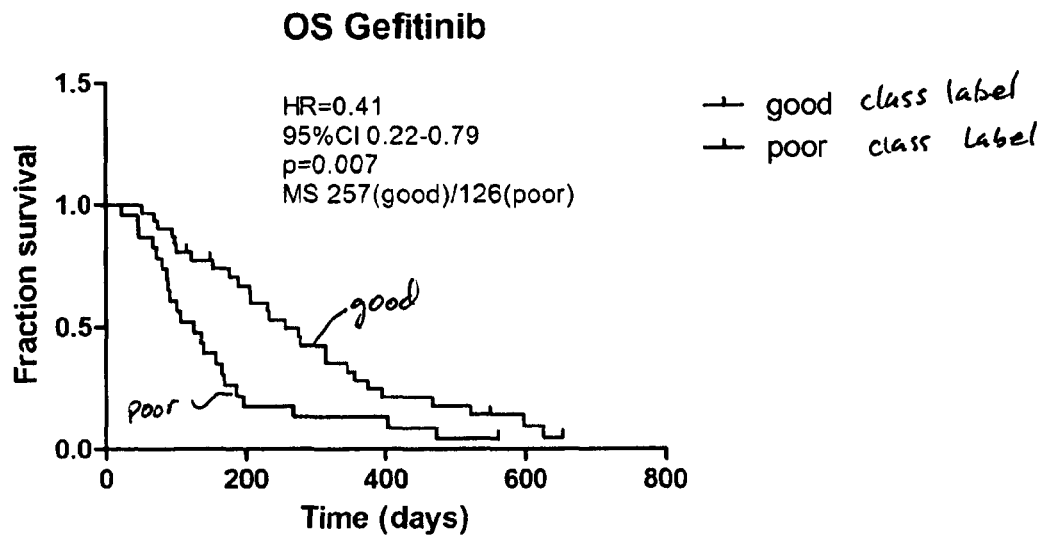
FIG. 2 is a Kaplan-Meier plot for a set of HNSCC patients treated with gefitinib and the class label assigned to serum samples using the method of FIG. 1. The plot indicates that patients labeled "good" had a better prognosis following treatment with gefitinib than the patients labeled "poor", with a hazard ratio of 0.41 (95% CI: 0.22-0.79) of good versus poor.

The methods described in this application have been applied to a set of 55 samples from HNSCC patients that were collected before treatment with gefitinib (tradename Iressa, AstraZeneca). Of these 31 yielded the label "good", 23 yielded the label "poor", and 1 resulted in the label "undefined". The analysis was performed in a fully blinded manner, i.e. no clinical data were available during the determination of the label. Once the labels were generated the clinical data were unblinded and a Kaplan-Meier analysis for overall survival could be performed from the clinical data for the endpoint overall survival. The Kaplan-Meier curves are shown in FIG. 2 for the patients labeled "good" and "poor". The patients labeled "good" had a better prognosis following treatment with gefitinib than the patients labeled "poor" with a hazard ratio of 0.41 (95% CI: 0.22-0.79) of good versus poor. The good and poor curves are statistically significantly different with a log-rank p-value of 0.007. These results indicate that the test described in this application can be used to separate HNSCC patients into groups with statistically different prognosis following treatment with gefitinib.

Figure 3:
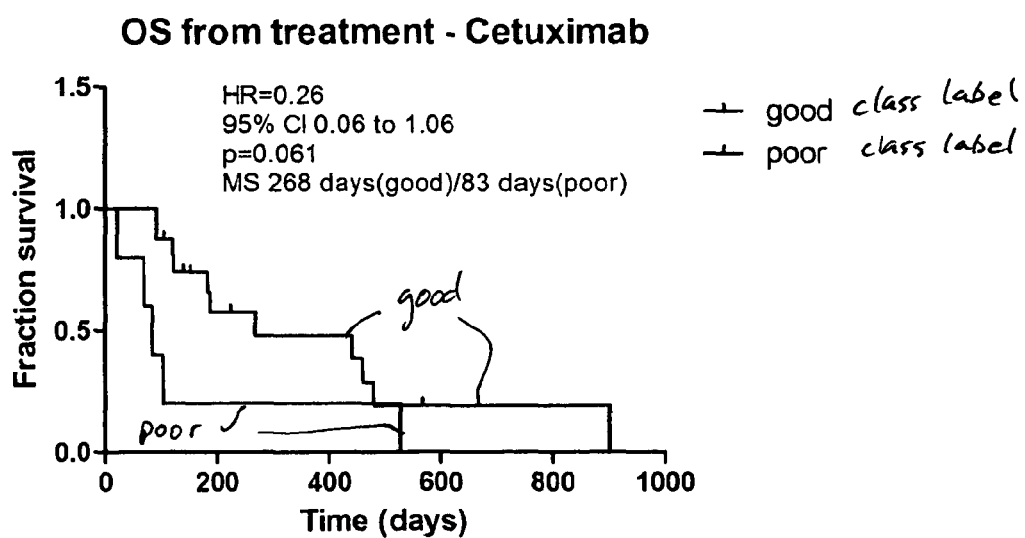
FIG. 3 is a Kaplan-Meier plot for a set of HNSCC patients treated with cetuximab and the class label assigned to serum samples using the method of FIG. 1. The plot indicates that patients labeled "good" had a better prognosis following treatment with gefitinib than the patients labeled "poor", with a hazard ratio of 0.26 (95% CI: 0.06-1.06) of good versus poor.

The methods described in this application have also been applied to a set of 21 samples from HNSCC patients that were collected before treatment with cetukimab (tradename Erbitux, Imclone). Of these 16 yielded the label "good" and 5 yielded the label "poor". The analysis was performed in a fully blinded manner, i.e. no clinical data were available during the determination of the label. Once the labels were generated the clinical data were unblinded and a Kaplan-Meier analysis for overall survival could be performed from the clinical data for the endpoint overall survival. The Kaplan-Meier curves are shown in FIG. 3 for the patients labeled "good" and "poor". The patients labeled "good" had a better prognosis following treatment with cetuximab than the patients labeled "poor" with a hazard ratio of 0.26 (95% CI: 0.06-1.06) of good versus poor. The good and poor curves are close to statistically significantly different with a log-rank p-value of 0.061. These results indicate that the test described in this application can be used to separate HNSCC patients into groups with statistically different prognosis following treatment with cetuximab.

From the above discussion, it will be appreciated that we have described a method of determining whether a HNSCC patient is likely to benefit from treatment with a drug targeting the EGFR pathway, comprising the steps of:

a) obtaining a mass spectrum from a sample from the patient;

b) performing one or more predefined pre-processing steps on the mass spectrum obtained in step a);

c) obtaining values of selected features in said spectrum at one or more predefined m/z ranges after the pre-processing steps on the mass spectrum in step b) have been performed; and d) using the values obtained in step c) in a classification algorithm using a training set comprising class-labeled spectra produced from samples from other patients to identify the patient as being likely to benefit from treatment with the said drug.

In preferred embodiments, the one or more m/z ranges comprises one or more m/z ranges selected from the group of m/z ranges consisting of:

5732 to 5795

5811 to 5875

6398 to 6469

11376 to 11515

11459 to 11599

11614 to 11756

11687 to 11831

11830 to 11976

12375 to 12529

23183 to 23525

23279 to 23622 and 65902 to 67502.

Preferably but not necessarily, the mass spectrum is obtained from a MALDI mass spectrometer.

The drug for which the patient is identified as being likely to benefit from may comprise a small molecule epidermal growth factor receptor tyrosine kinase inhibitor, such as getfitinib or erlotinib, or alternatively a monoclonal antibody epidermal growth factor receptor inhibitor such as cetuximab.

Variations from the particular details of the preferred embodiments disclosed are of course possible without departure from the scope of the invention. All questions of scope are to be determined by reference to the appended claims.

What is claimed is:

1. A method of determining whether a head and neck squamous cell carcinoma (HNSCC) patient is likely to benefit from treatment with a drug targeting the EGFR pathway, comprising the steps of:
    a) obtaining a mass spectrum from a blood-based sample from the HNSCC patient;
    b) performing one or more predefined pre-processing steps on the mass spectrum obtained in step a);
    c) obtaining integrated intensity values of selected features in said spectrum at one or more predefined m/z ranges after the pre-processing steps on the mass spectrum in step b) have been performed; and
    d) using the values obtained in step c) in a classification algorithm using a training set comprising class-labeled spectra produced from blood-based samples from other cancer patients to identify the HNSCC patient as being either likely or not likely to benefit from treatment with the said drug;
    wherein the drug targeting the EGFR pathway is selected from the group of drugs consisting of a small molecule epidermal growth factor receptor tyrosine kinase inhibitor and a monoclonal antibody epidermal growth factor receptor inhibitor.

2. The method of claim 1, wherein the one or more m/z ranges comprises one or more m/z ranges selected from the group of m/z ranges consisting of:

5732 to 5795

5811 to 5875

6398 to 6469

11376 to 11515

11459 to 11599

11614 to 11756

11687 to 11831

11830 to 11976

12375 to 12529

23183 to 23525

23279 to 23622 and 65902 to 67502.

3. The method of claim 1, wherein the mass spectrum is obtained from a MALDI mass spectrometer.

4. The method of claim 1, wherein the predefined pre-processing steps comprise a background subtraction step producing a background-subtracted spectrum, and a normalization step performing a normalization of the background-subtracted spectrum.

5. The method of claim 1, wherein the training set comprises class-labeled spectra produced from blood-based samples obtained from non-small cell lung cancer patients.

* * * * *